United States Patent
Kyne

(10) Patent No.: US 7,021,163 B2
(45) Date of Patent: Apr. 4, 2006

(54) APPARATUS AND METHOD FOR CONCURRENTLY MONITORING ACTIVE RELEASE AND PHYSICAL APPEARANCE OF SOLID DOSAGE FORM PHARMACEUTICALS

(75) Inventor: Oliver Kyne, Athlone (IE)

(73) Assignee: Elan Pharma International Limited, Shannon (IE)

( * ) Notice: Subject to any disclaimer, the term of this patent is extended or adjusted under 35 U.S.C. 154(b) by 0 days.

(21) Appl. No.: 10/492,098

(22) PCT Filed: Oct. 9, 2002

(86) PCT No.: PCT/IB02/04245

§ 371 (c)(1),
(2), (4) Date: Apr. 8, 2004

(87) PCT Pub. No.: WO03/034060

PCT Pub. Date: Apr. 24, 2003

(65) Prior Publication Data

US 2005/0003550 A1    Jan. 6, 2005

Related U.S. Application Data

(60) Provisional application No. 60/328,535, filed on Oct. 11, 2001.

(51) Int. Cl.
*G01N 33/00* (2006.01)

(52) U.S. Cl. ........................................ 73/866
(58) Field of Classification Search .................. 73/866; 366/158.5, 142, 165.2, 174.1
See application file for complete search history.

(56) References Cited

U.S. PATENT DOCUMENTS

| | | | |
|---|---|---|---|
| 2,322,087 A * | 6/1943 | Atwood | 366/165.2 |
| 3,430,925 A * | 3/1969 | Willy | 241/282.1 |
| 3,791,222 A | 2/1974 | Goodhart et al. | |
| 3,802,272 A * | 4/1974 | Bischoff et al. | 73/866 |
| 4,335,438 A | 6/1982 | Smolen | |
| 4,413,277 A * | 11/1983 | Murray | 348/86 |
| 4,506,985 A * | 3/1985 | Buchfink | 366/107 |
| 4,681,858 A * | 7/1987 | Chaudhari et al. | 436/165 |
| 4,855,821 A | 8/1989 | Swon et al. | |
| 4,856,909 A * | 8/1989 | Mehta et al. | 366/208 |
| 5,412,979 A * | 5/1995 | Fassihi | 73/53.01 |
| 5,589,649 A * | 12/1996 | Brinker et al. | 73/866 |
| 5,816,701 A | 10/1998 | Martin et al. | |
| 5,827,984 A | 10/1998 | Sinnreich et al. | |
| 6,174,497 B1 | 1/2001 | Roinestad et al. | |

FOREIGN PATENT DOCUMENTS

| | | | |
|---|---|---|---|
| EP | 635713 A1 * | 1/1995 |
| FR | 2722577 A1 * | 1/1996 |
| JP | 2001108668 | 4/2001 |
| JP | 2001108668 A * | 4/2001 |

* cited by examiner

*Primary Examiner*—Hezron Williams
*Assistant Examiner*—John Fitzgerald
(74) *Attorney, Agent, or Firm*—Synnestvedt & Lechner LLP

(57) ABSTRACT

An apparatus and method for monitoring the dissolution properties of a solid dosage form pharmaceutical or other material. The apparatus includes a hollow dissolution chamber for supporting the dosage form and subjecting it to a dissolution liquid so that the dosage form dissolves in the liquid. A dissolution liquid analyzing device (e.g., a spectrophotometer) analyzes the properties of the dissolution liquid as the dosage form dissolves. A video monitoring means (e.g., a stereo-microscope and video camera) provides a series of images of the dosage form as it dissolves. The series of images and data resulting from the analysis are recorded and correlated. The temperature, flow rate and chemical parameters of the dissolution liquid can be controlled (e.g., held constant or altered), if desired.

46 Claims, 3 Drawing Sheets

APPARATUS AND METHOD FOR CONCURRENTLY MONITORING ACTIVE RELEASE AND PHYSICAL APPEARANCE OF SOLID DOSAGE FORM PHARMACEUTICALS

CROSS-REFERENCE TO RELATED APPLICATION

This application claims the benefit U.S. Provisional Application No. 60/328,535 filed Oct. 11, 2001.

FIELD OF THE INVENTION

This invention relates generally to test apparatus and methods and more particularly to apparatus and methods for testing to determine the dissolution properties of solid dose form pharmaceuticals, agents and other materials.

BACKGROUND OF THE INVENTION

It is a well established practice in the pharmaceutical industry to test the dissolution properties of solid dosage form pharmaceuticals. The term solid dosage form as used herein means any dosage form, other than a liquid, and which can be delivered into the body of a being. Examples of such dosage forms are tablets, capsules, caplets, pills, suppositories, transdermal patches, etc. Moreover, the dosage forms may be immediate release or timed release.

As is known, dissolution is the process by which a solid substance dissolves in a solvent and is controlled by the affinity between it and the solvent. The sequence of events in a typical dissolution process entails several actions, e.g., the wetting of the dosage form, the subsequent penetration of the dissolution liquid into the dosage form, etc. Once this has occurred there are different modalities of release of the active ingredient(s) from the dosage form, such as erosion, diffusion, disintegration and combinations of those modalities.

Perhaps the primary reason for undertaking dissolution testing in the pharmaceutical industry is to measure the performance of a particular product. This is particularly important for oral solid dose forms of pharmaceuticals, but is not limited to oral dose forms, since release of the active ingredient(s) from the solid dose after oral administration is a prerequisite for absorption and bioavailability. Dissolution properties become even more significant if the solid dose form is of a sustained-release formulation, since dissolution is a key property of such a product.

Dissolution testing is also used as a key tool in research and development of new drugs since it can provide considerable information in the selection of an appropriate formulation for a proposed pharmaceutical. It also enables a manufacturer to accurately gauge the stability of a pharmaceutical to determine if it maintains its dissolution characteristics from the time of its manufacture to its expiry date.

In view of the above, and for other reasons as well, dissolution testing is now deemed of such importance that it is a mandatory United States pharmacopeial requirement. For example, the United States Pharmacopeial Convention presently identifies seven USP approved types of dissolution equipment for dissolution testing of solid dosage forms. Those types are referred to as USP I, USP II, USP III, USP IV, USP V, USP VI, and USP VII.

As is known USP I equipment is characterized by use of a rotating basket in which the solid dosage form of the pharmaceutical to be tested is held and immersed in a dissolution liquid in a flask or other concave bottom chamber. The flask or chamber typically has a volume of from 100 to 4000 ml. The basket is made up of a wire mesh of any mesh size, e.g., from USP mesh 10 to USP mesh 100. The basket is arranged to rotated about a vertical central axis at any suitable speed, e.g., from 50 to 125 rpm, within the dissolution liquid to enable the dissolution liquid to gain access to the solid dosage form to cause it to dissolve. With USP I equipment the dissolution liquid is sampled at a sampling point within the chamber, but outside the basket. The sample is provided to spectrophotometric, high performance liquid chromatographic or other suitable analyzer equipment for analysis.

While USP I apparatus may be generally suitable for their purposes, they nevertheless suffer from various significant disadvantages. One of the most significant disadvantages is the non-uniformity of the dissolution liquid in the chamber due to the production of poor eddy currents or inadequate stirring. Thus, within the chamber there are areas of the more concentrated dissolution liquid (so-called "hot spots") and areas of less concentrated liquid (so-called "blind spots"). In addition, the baskets of USP I equipment are relative fragile and can be bent or otherwise deformed, whereupon their rotation in a bent or deformed state-may result in uneven stirring of the dissolution liquid. Another significant disadvantage of this USP I equipment is that the baskets may become clogged, thereby impeding the access of the dissolution liquid to the dosage form. Lastly, USP I apparatus is not particularly suitable for testing the dissolution of a solid dosage form under changing pH conditions, e.g., conditions where pH increases, such as occurs when the dosage form is taken orally by a patient.

USP II equipment is similar to USP I equipment, except that the solid dosage form is placed at the bottom of the chamber and a paddle is used to stir the dissolution liquid in the chamber. In some applications a stainless steel or glass helix or another holder (sometimes referred to as a "lobster pot") may be used to encircle the solid dosage form and hold it slightly above the concave bottom surface of the chamber. The chamber typically has a volume of from 100 to 4000 ml. The paddle is disposed above the dosage form and is arranged to rotated about a vertical central axis at any suitable speeds, e.g., from 50 to 150 rpm to enable the dissolution liquid to have access to the dosage form to cause it to dissolve. The dissolution liquid is sampled within the chamber, but above the paddle and is provided to the same type of analysis equipment mentioned above for analysis.

While USP II apparatus may also be generally suitable for their purposes they also suffer from various drawbacks. One drawback is the non-uniformity of the dissolution liquid in the chamber due to the creation of a conical "blind-spot" of less concentrated dissolution liquid directly under the paddle. Another drawback is that the dosage form is susceptible to floating, if not held in position by a helix or lobster pot, thereby interfering with its even dissolution. Moreover, since the dosage form is exposed, it can be struck by the paddle, possibly breaking the dosage form and thus interfering with its normal dissolution properties. Further still the dosage form may rest on or stick to the inner surface of the chamber, thereby reducing the surface area of the dosage form so that an accurate reading of its dissolution properties is compromised. The use of a helix, lobster pot or other device to surround the dosage form to lift it off the surface of the chamber may eliminate that problem, but is not conducive for use with dosage formulations that swell, e.g., hydrogels. Moreover, like USP I apparatus, USP II apparatus is not particularly suitable for testing the dissolution of a solid dosage form under changing pH conditions USP III equipment is sometimes referred to as a "reciprocating cylinder" and is particularly suited for extended release products. USP III equipment basically comprises an array of plural rows of individual flat bottomed glass vessels or chambers for holding the dissolution liquid. The vessels are typically of a volume of 200 ml. A plurality of reciprocating cylinders having mesh tops and bottoms into which respective ones of solid dosage forms of the pharmaceutical are located are disposed over the array of vessels for reciprocation and immersion in selected rows of the array of vessels. For example, the reciprocating cylinders may be reciprocated into the first row of the array of vessels to immerse the dosage forms into the dissolution liquid in those vessels. Thereafter the row of cylinders can be reciprocated out of the first row of vessels and indexed to the next successive row of vessels to immerse the dosage forms into the dissolution liquid in the second row of vessels. This operation can continue until all of the rows of vessels have been used. The advantage of this type of equipment is that each row of vessels may include dissolution liquid of the same pH or of increasing pH. Moreover, the fact that this type of apparatus uses plural vessels into which each dosage form is immersed enables the apparatus to be used to test poorly soluble active ingredients, since there will be more dissolution liquid available to dissolve such formulations than exists in either USP I or USP II equipment. Notwithstanding these advantages, the USP III apparatus still suffer from various disadvantages. For example, poorly soluble formulations which disintegrate could experience a loss of sink conditions if disintegration occurs in one sample 250 ml tube. Moreover, the apparatus is difficult to use with a surfactant based dissolution liquid, as frothing of the liquid severely limits the sample holder reciprocation rate. Further still, clogging of the sample holder mesh is possible, thus obstructing the free flow of dissolution liquid past the sample formulation.

USP IV equipment is sometimes referred to as a "flow through cell" and is particularly suitable for testing poorly soluble drugs and for extended release products. Moreover, UPS IV apparatus is suitable for testing active substances, granulated substances and formulated dosages in the same equipment. To that end USP IV equipment basically comprises a reservoir and a pump for the dissolution liquid, a flow-through-cell and a water bath for maintaining the temperature of the dissolution liquid. The cell is a hollow cylinder having a conical bottom wall with a central opening forming the inlet to the cell. The dosage form to be tested is disposed in the center of the cell. The top end of the cell is in the form of a filter or sieve. The dissolution liquid is pumped into the bottom of the cell so that it flows past the dosage form to cause it to dissolve. The dissolution liquid exits through the filter at the top of the cell. Since this equipment exposes the dosage form to a flow of the dissolution liquid past it, the dosage form is always subjected to fresh dissolution liquid, making the equipment particularly suitable for low solubility drugs. Moreover, this equipment enables one to precisely change the pH of dissolution liquid and avoids the hot spots and blind spots that are inherent in USP I and USP II equipment. Notwithstanding these advantages, USP IV equipment still suffers from its own disadvantages, e.g., it requires large volumes of dissolution liquid, calibration tests are unavailable, and validation of the flow rate is difficult.

USP V equipment is sometimes referred to as a "paddle over disk apparatus." It basically comprises the USP II equipment with the inclusion of a stainless steel disk located at the bottom of the chamber. The disk is arranged to hold a transdermal dosage form. While USP V equipment offers advantage over USP II equipment for transdermal dosage forms, it never the less suffers from the same disadvantages of that equipment insofar as the non-uniformity of the dissolution liquid in the chamber is concerned.

Other USP approved equipment is USP VI equipment (sometimes referred to as a "cylinder" apparatus), and USP VII equipment (sometimes referred to as a "reciprocating holder" or "reciprocating disk" apparatus). As is known USP VI apparatus basically comprises the USP I equipment, except that the mesh basket is replaced with a stainless steel cylinder stirring element. USP VII equipment is sometimes referred to as a "reciprocating holder" or "reciprocating disk" apparatus and basically comprises a set of volumetrically calibrated glass cylinders.

The patent literature also discloses various devices for testing the dissolution of solid dosage forms. See, for example, U.S. Pat. No. 4,855,821 (Swon et al.), U.S. Pat. No. 4,856,909 (Mehta et al.), U.S. Pat. No. 5,127,278 (Benz), U.S. Pat. No. 5,142,920 (Bart et al.), U.S. Pat. No. 5,412,979 (Fassihi), U.S. Pat. No. 5,469,752 (Kitamura et al.), U.S. Pat. No. 5,816,701 (Martin et al.), U.S. Pat. No. 5,827,984 (Sinnreich et al.), U.S. Pat. No. 5,908,995 (Pauchon et al.), U.S. Pat. No. 6,076,411 (Horvath), U.S. Pat. No. 6,163,149 (Löfler), U.S. Pat. No. 6,170,980 (Martin) and U.S. Pat. No. 6,174,497 (Roinestad et al.) and Japanese Abstract JP05184579A2.

The patent to Martin et al. discloses an automated tablet dissolution apparatus that includes a camera under computer control for viewing the contents through the bottom of a dissolution vessel. A tablet to be tested is located with a basket disposed in the dissolution vessel and is exposed to a heated dissolution media the vessel. The camera is used to determine if the tablet was dropped into the dissolution vessel properly or has dissolved properly or to enable the contents of the vessel to be visually inspected. This testing of a sample of the dissolution media over a period of time is achieved in this patent by various techniques, e.g., spectrophotometry, high performance liquid chromatography, etc.

The patent, to Swon et al. (U.S. Pat. No. 4,855,821) discloses an apparatus for dissolution testing solid dosage forms, e.g., tablets, including one or more video cameras for the surveillance of a plurality of separate tablet containing vessels to record the dissolution of the tablets in a liquid dissolution media. Plural tablets are held on a wire mesh or screen.

The patent to Löfler (U.S. Pat. No. 6,163,149) discloses an apparatus for dissolution testing of medicaments in pressed form, such as tablets, pills, or capsules, and makes use of a basket-like frame supporting plural glass tubes, each of which is adapted to hold the medicament.

The patent to Martin (U.S. Pat. No. 6,170,780) is similar to U.S. Pat. No. 5,816,701 which was discussed above.

While all of the above identified apparatus and methods of use may be suitable for their intended purposes they still leave much to be desired from the standpoint that the information about the dissolution properties of the solid dosage forms that can be determined by their use is somewhat limited. In this regard prior art apparatus and techniques may enable one to determine the rate at which a particular solid dosage form dissolves (i.e., its so-called "dissolution profile"), but they do not provide accurate information about the mechanism of how the dosage form actually dissolved, e.g., by erosion, disintegration, diffusion and/or combinations of those actions. Moreover, while some prior art dissolution testing systems may have included utilizing a visualization device, e.g., a camera to record selected images of the dosage forms during their process of dissolving, such techniques have been very limited in the quality of the images provided, particularly where the dosage forms are susceptible to movement and displacement in the apparatus as they dissolve. For example, as is known the rotating paddles of USP II devices tend to cause the dosage forms to shift around and move in the dissolution vessel, thereby making sustained, accurate imaging difficult. Moreover, the stirring of the dissolution liquid causes surface turbulence, rendering image acquisition through the surface difficult. The rotating basket of USP I apparatus also presents an imaging problem since the basket in which the dosage form is located is moving and a relatively high speed, thereby tending to blur or otherwise obscure the dosage form during the dissolution process. Further still, where the dosage form is a sustained or timed release medication, e.g., a capsule with a large plurality of polymer coated active ingredient beads, with some of the beads having thicker coatings than others to enable the timed release of their active ingredient(s), the prior art systems have proved wanting to provide high quality images of the entire dissolution process from which accurate information about the manner and rate of release of the active ingredient(s) can be determined.

SUMMARY OF THE INVENTION

An apparatus and method for monitoring the dissolution properties of a solid dosage form pharmaceutical (e.g., capsule, tablet, pill, suppository, transdermal patch, etc.) or other agent or material having at least one active ingredient.

The method consists of disposing a solid dosage form in a chamber and introducing a dissolution liquid into the chamber to cause the dosage form to dissolve in the dissolution liquid. The dissolution liquid is analyzed as the dosage form dissolves in the dissolution liquid to determine the dissolution properties of the dosage form. A series of images of the dosage form is provided simultaneously with the analysis of the dissolution liquid.

In accordance with one exemplary aspect of the invention the temperature of the dissolution liquid is controlled.

The apparatus of this invention comprises a dissolution chamber, video monitoring means (e.g., a video camera and stereo-microscope, etc.), and dissolution liquid analyzing means (e.g., spectrophotometric, high performance liquid chromatography, etc. equipment). The dissolution chamber comprises a hollow vessel (e.g., a hollow body having a flat bottom wall, a circular sidewall, a baffle and an evaporation cover or lid). A dosage form support (e.g., a wire mesh) is located within the interior of the chamber. The chamber includes an inlet and outlet coupled to the interior of the chamber (e.g., the inlet and outlet are located in the side wall of the chamber, with the baffle located adjacent the inlet). The support is arranged to support the dosage form in the chamber within a predetermined visualization field in the chamber.

The inlet of the chamber is adapted to enable a dissolution liquid to enter the chamber and flow gently through the interior of the chamber for exposure to the dosage form. The support and the gentle flow of the dissolution liquid tend to prevent displacement of the dosage form from said visualization field. The flow of the dissolution liquid causes the dosage form to dissolve in the dissolution liquid. The outlet of the chamber is coupled to the analyzing means so that a sample of the dissolution liquid can be analyzed by the analyzing means to determine the properties of the dissolution liquid. The video monitoring means is adapted for aiming at the visualization field to provide a series of high quality images, e.g., a continuous video image, of the dosage form simultaneously with the analysis of the dissolution liquid by the analyzing means.

DETAILED DESCRIPTION OF THE PREFERRED EMBODIMENT

Figure 1:
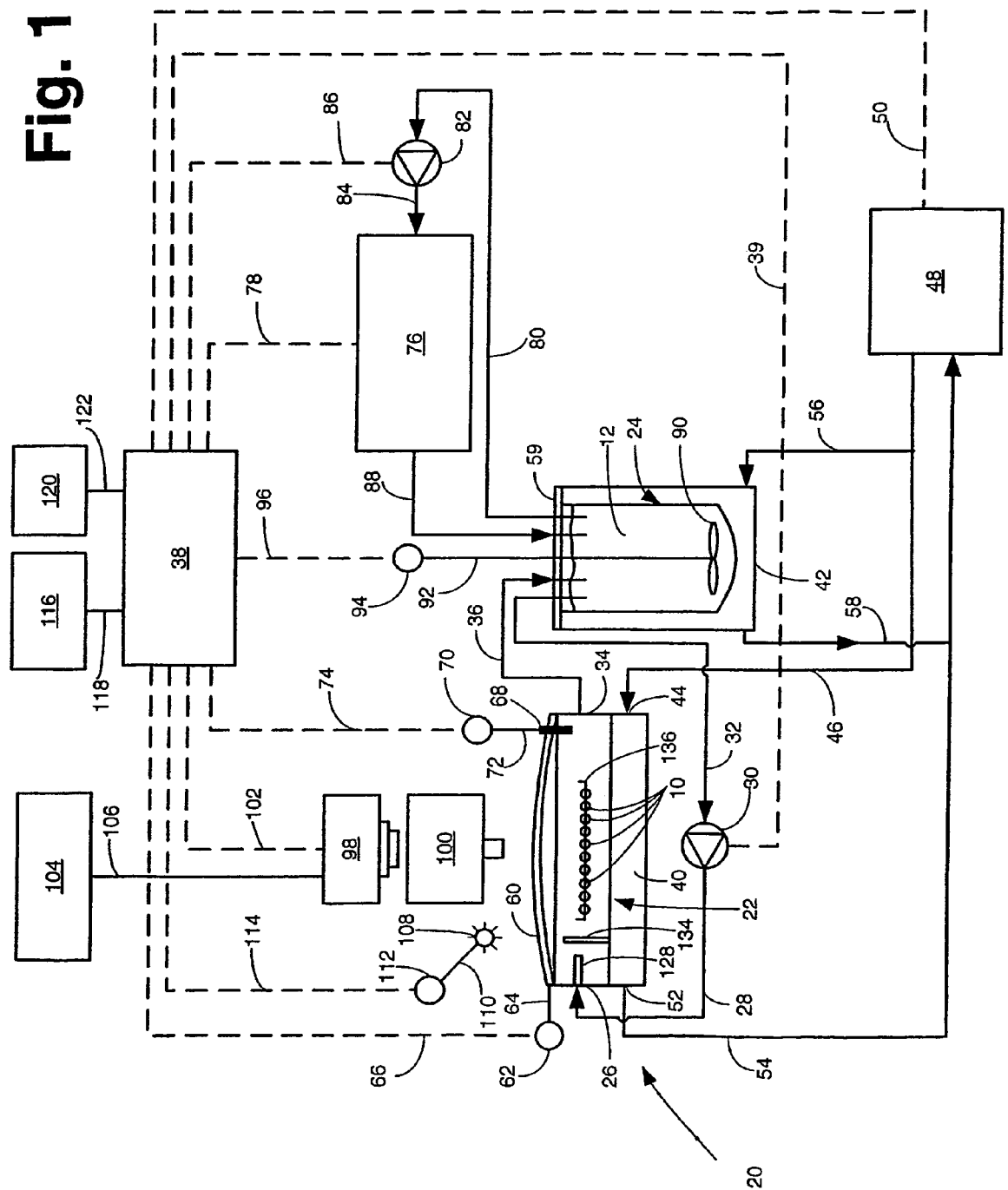
FIG. 1 is a schematic diagram of one exemplary embodiment of a system constructed in accordance with this invention.

Referring now to the various figures of the drawing wherein like reference characters refer to like parts, there is shown in FIG. 1 one exemplary embodiment of a system 20 for concurrently monitoring active release and physical appearance of solid dosage form pharmaceuticals constructed in accordance with this invention.

The system 20 includes a dissolution chamber 22, whose details will be described later with reference to FIGS. 2 and 3, into which at least one, but preferably a plurality of solid dosage form pharmaceuticals 10 are disposed for exposure to a dissolution liquid 12. The dosage forms 10 are located within a predetermined position within the chamber 22 in an area which defines a visualization field (to be described later). The dissolution liquid 12 is provided into the chamber 22 from a dissolution liquid reservoir 24. The details of the reservoir 24 will also be described later. Suffice it for now to state that the reservoir 24 is a hollow member for holding a quantity, e.g., 1000 ml, of the desired dissolution media 12, e.g., purified water, a phosphate buffer with a pH of 6.8, 0.01 normal hydrochloride solution, or any other liquid known for use in dissolution testing and which is preferably transparent (for reasons to be appreciated later). The dissolution chamber 22 is arranged to receive the dissolution liquid from the reservoir 24 and to return it to the reservoir. In particular, the dissolution chamber includes an inlet 26 connected via a line or conduit 28. The conduit 28 is connected to the output of a peristaltic pump 30. In accordance with one exemplary embodiment of this system 20, the pump is available from Icalis Data Systems of the U.K. under the model designation PCP490. The input to the pump 30 is provided via a line or conduit 32 extending into the interior of the reservoir 24. The pump is operated at any desirable speed, e.g., 1 to 200 rpm. The dissolution chamber also includes an outlet 34. That outlet is connected via a gravity return line or conduit 36 back to the reservoir 24. The pump 30 is operated under control of a computer 38 via electrical lines 39. When the pump 30 is operated the dissolution liquid 12 within the reservoir 24 is pumped via lines 32 and 28 and inlet 26 so that it flows into the interior of the dissolution chamber 22. Accordingly, the plural solid dosage forms 10 to be tested that are located within the chamber are exposed to the dissolution liquid, so that they can begin to dissolve, thereby releasing their active ingredient(s) into that liquid. As will be described in detail later, the dissolution chamber is constructed in such a manner that the flow of dissolution liquid through it is sufficiently gentle so that the flow does not disturb the solid dosage forms 10 from their position in the visualization field, while still providing sufficient mixing of the liquid in the chamber ensure substantial uniformity of concentration . The dissolution liquid with the dissolved active ingredient(s) is returned to the reservoir 24 via the dissolution chamber's outlet 34 and the associated return line 36. This operation is effected on a continuous basis under the control of the computer 38, as will be described in detail later.

In accordance with one preferred aspect of the invention, the temperature of the dissolution liquid 12 is controlled, e.g., maintained at a predetermined temperature, such as body temperature 37° C. To that end, in the exemplary embodiment shown in FIG. 1, the system 20 includes two temperature control devices, e.g., water jackets 40 and 42, whose details will be described later. Suffice it for now to state that the jacket 40 is disposed contiguous with, e.g., below, the dissolution chamber 22, while the jacket 42 is disposed contiguous with, e.g., surrounding the liquid reservoir 24. The water jacket 40 is a hollow member which includes an inlet 44 to which a line or conduit 46 is connected. The line 46 is connected to a source of heated water, e.g., a heating unit 48. In accordance with one exemplary embodiment of this system 20, the heating unit 48 is available from Neslab Instruments, Ltd. of the U.S.A. under the model designation R-134A. The heating unit 48 includes its own pump (not shown) and is arranged to heat a supply of water to bring the water to a desired temperature, e.g., 38° C., and to maintain it at that temperature under the control of the computer 38. To that end the heating unit 48 is arranged to heat the water to any desired temperature within the range of 25° C.–50° C. and at a rate of up to 5 liters per minute. The heating unit is connected to the computer via electrical lines 50. The water jacket 40 includes an outlet 52 which is connected to a line or conduit 54. The line 54 is connected to the heating unit 48 to return the water from the jacket 40 back to the heating unit for reheating. It should be pointed out at this juncture that heat dissipation properties of the conduit 46 carrying the water to the jacket 40 and the heat dissipating properties of the jacket 40 are such that water heated to 38° C. in the heater unit is kept at a temperature of 37° C. in the jacket 40 of the dissolution chamber to hold the dissolution liquid 12 in the chamber 22 at that temperature.

The liquid reservoir's water jacket 42 includes an inlet line or conduit 56, which is a branch of the inlet line 46, for carrying the heated water from the heating unit 48 to the interior of the jacket 42. The jacket 42 also includes an outlet line or conduit 58, which is a branch of line 54, returning the water to the heating unit 48. Accordingly, heated water from the heating unit 48 is pumped through lines 46 and 56 into the water jackets 40 and 42, respectively, to heat the dissolution chamber 22 and the reservoir 24, respectively, under control of the computer 38. The liquid reservoir includes a cover 59 to prevent evaporation of the liquid therein. This cover includes various opening through which the various lines or conduits carrying the dissolution liquid to and from the dissolution chamber and carrying the dissolution liquid sample to and from the system's analyzer (to be described later) extend. Thus, evaporation of the dissolution liquid from the reservoir (which serves as the source for the liquid sample to be analyzed), and which could result in concentrating the dissolution liquid to give false dissolution data, is deterred by the presence of the lid 59.

Evaporation of the dissolution liquid from the dissolution chamber 22 is similarly deterred by the presence of an evaporation lid or cover 60 disposed over the dissolution chamber. The details of the cover or lid 60 will be described later. Suffice it for now to say that the lid 60 is preferably a heated member, e.g., a transparent glass member which includes transparent electrically operated heating elements (not shown). In accordance with one exemplary embodiment of this system 20, the heated cover is available from Pilkington in the U.S.A. under the model designation TEC-GLASS™. The electrically heated cover 60 is connected to an electrical controller 62 via electrical lines 64. The controller 62 is, in turn, electrically connected to the computer 48, via electrical lines 66, and is controlled thereby.

In order to monitor the temperature within the interior of the dissolution chamber 22 the system 20 includes a temperature probe 68, e.g., a thermocouple. The probe 68 extends through the dissolution chamber cover 60 into the interior of the dissolution chamber for immersion in the dissolution liquid 12. The probe 68 is electrically connected to an electrical controller 70 via electrical lines 72. In accordance with one exemplary embodiment of this system 20, the thermocouple and associated controller is available from Hanna Instruments, Ltd. of the U.K. under the model designation Hi-93531. The controller 70 is in turn electrically connected to the computer 38, via electrical lines 74, and is controlled thereby.

In order to monitor the parameters of the dissolution liquid during the dissolution test procedure, the system includes a dissolution liquid analyzer 76. In the exemplary embodiment the analyzer 76 is a UV spectrophotometer. In accordance with one exemplary embodiment of this system 20, the spectrophotometer is available from Unicam, Ltd. of the U.K. under the model designation UV3-200. Other conventional spectrophotometric or other analyzers, such as a high performance liquid chromatograph, can be used as well. In the system 20 shown in FIG. 1 the analyzer 76 is arranged to continuously receive a sample of the dissolution liquid 12 from the dissolution chamber 22, whereupon the sample flows through the analyzer 76. The analyzer provides data representative of the percentage of the active ingredients dissolved in the dissolution liquid as the sample flows past its sensors (not shown), as is conventional. The computer 38 controls the operation of the analyzer 76 via electrical lines 78 and receives the data output from the analyzer via those electrical lines.

The dissolution liquid sample is provided into the analyzer 76 via a conduit or line 80 extending into the reservoir 24. This sample outlet line 80 is connected to the input of a pump 82. In accordance with one exemplary embodiment of this system 20, the pump 82 is available from Icalis Data Systems of the U.K. under the model designation PCP490. The outlet of the pump is connected via a conduit 84 to the input of the analyzer 76. The operation of the pump 82 is controlled by the computer 38 via electrical lines 86. The liquid sample is returned from the analyzer back to the reservoir 24 via a line or conduit 88.

Since the analyzer 76 receives the dissolution liquid 12 sample from the interior of the liquid reservoir 24, it is of considerable importance that the liquid within the reservoir be of a uniform concentration. To that end, the system 20 includes a stirring paddle or propeller 90 mounted on a rotating shaft 92 extending into the interior of the reservoir 24. The shaft 92 is connected to an electrical motor or rotary driver 94, which is connected to the computer 38 via electrical lines 96. In accordance with one exemplary embodiment of this system 20, the electric motor 94 is available from Stuart Scientific, Ltd. of the U.K. under the model designation SS3. The speed of rotation of the paddle/propeller 90, e.g., 1 to 2500 rpm, is controlled by the operation of the computer to stir the liquid within the reservoir so that it is uniform throughout.

As mentioned earlier in order to provide additional valuable information regarding the dissolution properties of the solid dose forms 10, the system 20 makes use of imaging means which is arranged to operate concurrently with the analyzer so that a series of images taken by the imaging means can be coordinated with the data resulting from the operation of the analyzer 76. In the embodiment shown the imaging means basically comprises a video camera 98 and an associated stereo-microscope 100. In accordance with one exemplary embodiment of this system 20, the video camera 98 is available from JVC (Victor Company of Japan, Ltd.) under the model designation TK-C1381EG and the stereo-microscope is available from Helmut Hudd, GmBH of Germany under the model designation SM33. The stereo-microscope 100 is located adjacent the dissolution chamber 22 so that the plural solid dosage forms 10 within the dissolution chamber 22 are in the microscope's field of view or visualization field. The stereo-microscope provides an enlarged stereo image (e.g., from 5× to 45×) of the dosage forms in the visualization field at its eyepiece. The video camera 98 is mounted adjacent the microscope's eyepiece so that it can record the enlarged stereo image of the dosage forms as they dissolve during the dissolution test. The camera 98 is connected to the computer 38 via electrical lines 102, so that the computer can control its operation. A photo-printer 104 is connected to the video camera 98, via electrical lines 106, to provide a hard copy print of the any one of the series of images taken by the camera. The output of the camera 98 can be fed directly into the computer 38 for storing the images therein, e.g., on a hard disk drive associated with the computer.

In any case, the images of the dosage forms showing their condition at any point in their dissolution cycle can be correlated by an operator of the system with the data received from the analyzer to provide valuable information regarding the dissolution properties of the dosage forms. This operation will be described later. In fact, the computer 38 may include software for automatically analyzing the images provided by the video camera to produce data representing those images for comparison, correlation and analysis with the data provided by the analyzer 76, thereby resulting in an automatic dissolution testing system.

It should also be pointed out that the series of images captured by the video camera can be provided back to the computer through some other means than that shown, e.g., if the video camera utilizes videotape or some other media, e.g., a solid state memory device, a CD or some other recordable medium, the medium bearing the images can be input into the computer through any conventional technique. Moreover, the series of images need not be coordinated by the computer at all. Thus, the system of this invention contemplates manual viewing the series of images and the data to draw conclusions therefrom.

In order to ensure that the video camera 98 has sufficient light to provide a good quality image of the dosage forms as they dissolve, the system 20 may include a lamp or other light source 108 disposed adjacent to the lid 60 of the dissolution chamber 22 so that the light produced thereby can illuminate the dosage forms 10 within the chamber. The lamp 108 is connected via electrical lines 110 to an electrical power supply 112, which is in turn connected via electrical lines 114 to the computer 38. Accordingly, the light output from the lamp 108 can be controlled by the computer and directed through the evaporation lid to evenly and brightly illuminate the visualization field. If a stereo-microscope is utilized in the system 20 and it includes its own light source, as does the exemplary stereo-microscope of Helmut Hudd, GmBH disclosed above, a separate lamp 108 and its associated power supply need not be used.

The system 20 includes a second, data printer 116 connected to the computer 38 via electrical lines 118. The printer 116 is arranged to be controlled by the computer for providing hard copies of the data produced by the analyzer, and if desired for providing hard copies of the images captured by the video camera (e.g., to accomplish the same function as provided by the photo printer 104). In accordance with one exemplary embodiment of this system 20, the second printer 116 is available from Mitsubishi Electric Corporation of Japan under the model designation CP700E (B).

In order to start any particular dissolution test, the system 20 can include a start switch 120, connected to the computer 38 via electrical lines. Alternatively, the computer may provide the start signal for initiating any test procedure by depression of a suitable keyboard key or by mouse activation.

Figure 2:
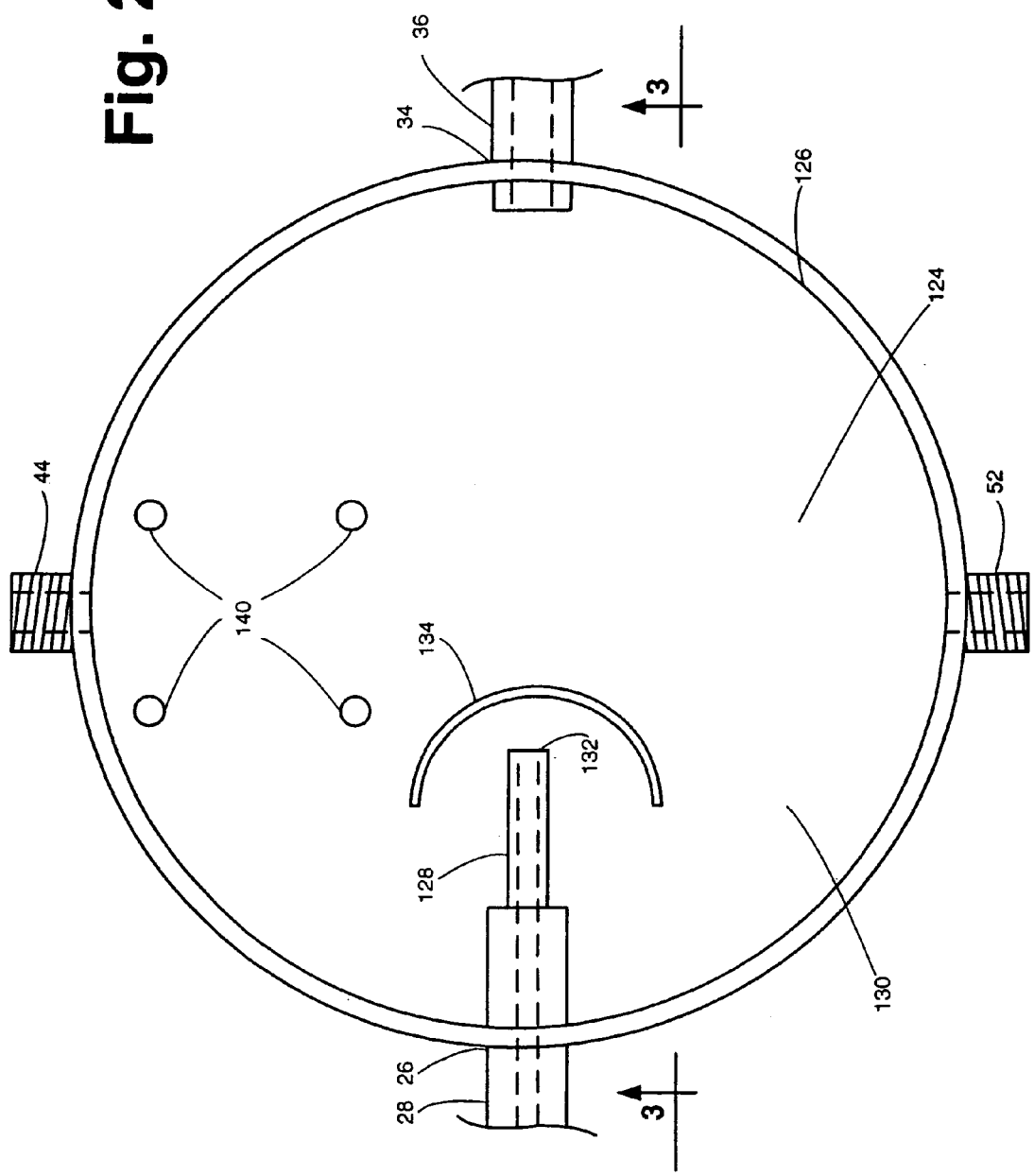
FIG. 2 is a top plan view of the dissolution chamber shown in FIG. 1, but with the evaporation lid removed.
Figure 3:
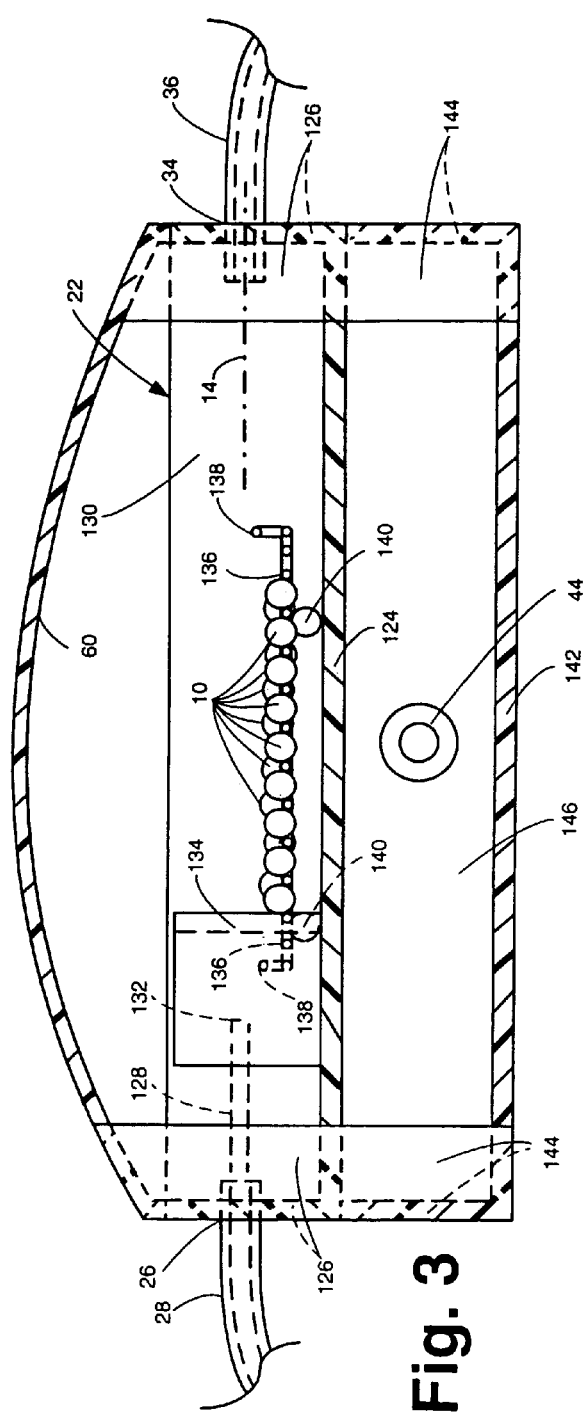
FIG. 3 is an enlarged sectional view taken along lines 3—3 of FIG. 2 and also showing the solid dosage form support structure, e.g., a mesh screen, disposed therein.

Referring now to FIGS. 2 and 3 the details of the dissolution chamber 22 and its associated water jacket 40 will now be described. The dissolution chamber 22 basically comprises a petri dish-like hollow member having a generally planar bottom wall 124 of a circular periphery and from which a circular sidewall 126 projects upward. The top surface of the sidewall 126 lies in a common plane parallel to the bottom wall 124. The heretofore identified inlet 26 to the chamber 22 is in the form of horizontally disposed nozzle 128 extending into the interior 130 of the chamber 22 and terminating at an open end 132. The nozzle includes a central passageway (not shown) in fluid communication with the conduit or line 28 carrying the dissolution liquid from the reservoir 24. Disposed in front of the nozzle's outlet 132 is an upstanding arcuate wall forming a baffle 134 against which the flow of dissolution liquid 12 entering the chamber's interior 130 is directed. The outlet 34 of the chamber is located in the sidewall 128 diametrically opposed to the inlet 26. In accordance with one exemplary embodiment of this system 20, the diameter of the bottom wall 124 is 90 mm, the height of the sidewall 126 is approximately 20 mm, with the inlet and outlet each being located halfway up from the bottom wall, i.e., 10 mm from the bottom wall.

Figure 4:
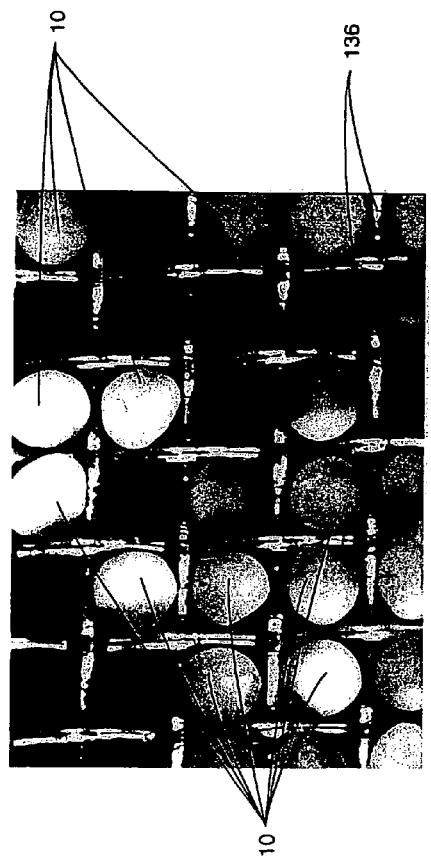
FIG. 4 is a portion of a photomicrograph showing a plurality of solid dosage forms disposed on the mesh screen of the dissolution chamber of FIG. 1 after those dosage forms have begun to dissolve, which image is representative of a single frame of the series of images provided by the video monitoring means shown in FIG. 1.

As best seen in FIGS. 3 and 4 the plural dosage forms 10 are arranged to be supported in the interior 130 of the chamber 22 by a support means in the form of a wire mesh 136. The mesh is a generally flat member of approximately square shape, although other shapes can be used as well, formed of intersecting stainless steel wires and having slight upstanding peripheral wall 138. The various solid dosage forms to be tested are placed on the mesh, with each dosage form being disposed in its own respective interstitial space created between the crossing wires forming the mesh (see FIG. 4). The mesh is itself supported slightly off of the inner surface of the bottom wall 124 via a plurality of spherical legs 140 fixedly secured to the bottom wall of the chamber. This arrangement ensures that the dissolution liquid flowing into the chamber call flow all about the dosage forms, from under, over and around their sides. The support mesh 136 can be of any mesh size within the range of USP mesh 10 to USP mesh 100.

As best seen in FIG. 2 the support legs 140 are arranged in a square array located immediately adjacent the sidewall 126 between the inlet 26 and outlet 34 and spaced from the center of the chamber 22. Accordingly, the mesh support 136 with the dosage forms 10 thereon is out of the way of direct impingement from the dissolution liquid 12 exiting the nozzle 128. In particular, the liquid exiting the nozzle's open end 132 impinges the inner surface of the baffle 134 from whence it spreads out, slowing in velocity, and flows gently around the baffle on one side to engage and flow past the dosage forms on the mesh 136, while another portion flows about the other side of the baffle. The flows merge, mix and then exit the chamber through the outlet 34.

In accordance with a preferred operation of the system 20 the rate of flow of dissolution liquid 12 into the chamber is controlled by the pump 30 via signals from the computer 38 to ensure that the liquid fills the chamber only up to the height of the outlet 34 and into the outlet, but not completely submerging the outlet as shown by the liquid level line 14 in FIG. 3. The surface tension of the dissolution liquid 12 ensures that it flows through the outlet into the return line 36, while enabling air to escape from that line above the liquid level. Accordingly, the dissolution liquid flows back to the reservoir uniformly under the influence of gravity. In this exemplary arrangement the volume of dissolution liquid within the dissolution chamber is approximately 28 ml.

As should be appreciated by those skilled in the art, the spreading of the dissolution liquid throughout the interior of the chamber as just described effectively mixes the liquid within that chamber. Accordingly, the incoming and less concentrated dissolution liquid 12 is sufficiently mixed with the liquid in the chamber to ensure consistent dissolution of the dosage forms, all without disturbing the position of the dosage forms from within the camera's visualization field. Moreover, the gentle flow of the liquid through the chamber ensures that the surface of the liquid 12 in the chamber 22 is relatively smooth and non-turbulent so that it does not interfere with the imaging of the dosage forms by the camera through it and the liquid in which the dosage forms are submerged.

It should be pointed out at this juncture that the support mesh 136 with the solid dosage forms thereon can be located in the interior of the chamber at a diametrically located position than that shown in FIG. 2, i.e., immediately adjacent the sidewall between the inlet and outlet on the opposite portion of the sidewall, if desired. Location of the mesh at either the center of the chamber or adjacent its outlet is not particularly desirable.

As best seen in FIGS. 1 and 3, the evaporation lid 60 is a dome-shaped member of the same outside diameter as the chamber 22 and is arranged to be disposed on the top edge of the chamber's sidewall 126. The dome shape of the lid ensures that any dissolution liquid that should condense on its inner surface (notwithstanding the fact that the lid is heated) will run down the arcuate inner surface of the lid and down the inner surface of the chamber's sidewall, thereby preventing dropping into the center of the chamber, since such action could result in agitation of the surface of the liquid at the visualization field, thereby impeding the acquisition of good images of the dosage forms as they dissolve. The evaporation lid is formed of a transparent material, e.g., glass, to enable the camera to visualize the solid dosage forms through it and the liquid 12 in which those forms are immersed.

The water jacket 40 basically comprises a petri dish-like hollow member having a generally planar bottom wall 142 having a circular periphery from which a circular sidewall 144 projects upward. The top surface of the sidewall 144 lies in a common plane and is secured to the undersurface of the dissolution chamber's bottom wall 124, thereby forming an enclosed hollow interior 146. The heretofore identified inlet 44 to the water jacket extends through the sidewall 144 immediately under the location of the support mesh 136 in the chamber 22 located above the jacket. The outlet 52 of the water jacket 42 is located in the sidewall 144 diametrically opposite the inlet 44 as best seen in FIG. 2. Accordingly, hot water introduced into the inlet flows through the chamber, whereupon its heat is picked up through the dissolution chamber's bottom wall 124 to ensure that the temperature of the dissolution liquid in the dissolution chamber is maintained at the desired temperature, e.g., 37° C.

It should be pointed out at this juncture that the control of the dissolution liquid temperature need not entail heating of the same, but, may entail cooling for some applications. In such a case water jackets or other temperature control devices utilizing some cooling medium can be utilized. In fact, any other means for either raising or lowering the temperature of the dissolution liquid in the dissolution chamber and/or in the liquid reservoir can be utilized in accordance with the teachings of this invention. Moreover, the temperature control, if any, need not be accomplished on a continuous or even repetitive basis, but may be used as needed. Also the composition of the dissolution liquid may be changed during the dissolution testing operation, e.g., a dissolution liquid of one pH can be used for a portion of the cycle of testing and then a dissolution liquid of a higher or lower pH can be used at a later part of the cycle.

In FIG. 4 there is shown a photograph of a mesh supporting a plurality of solid dosage forms of a solid dosage form pharmaceutical taken from the series of images produced by the system 20 of this invention and which photograph can be compared to the data provided by the analyzer 76 at the time of that photograph. With that information the person studying the photograph and data can determine the mechanism of dissolution and if there are any anomalies present.

The following constitutes one exemplary operation of the system 20. The user first switches on the water heater unit 48 to heat the reservoir 24 and the dissolution media located therein. For example, if the dissolution liquid is water, the user takes a vial of water and degasses it with helium to remove any dissolved air which could pose dissolution problems. When the water is degassed sufficiently it is poured into the reservoir 22 and the stirrer 90 is turned on to stir that liquid around gently. Then the inlet and outlet conduits 80 and 88, respectively, for the analyzer 76 are extended through respective openings in the reservoir's cover 59. So too, the inlet and outlet 26 and 34, respectively, of the dissolution chamber 22 are extended through respective openings in the reservoir cover 59. Once this is done the pump 30 for the dissolution chamber 22 is turned on to carry the water 12 into the chamber 22 to fill it to the height 14 at the outlet 34, whereupon the water exits through the outlet and the return line 36 to the reservoir 24. Once this has been accomplished, the pump 82 coupled to the input of the analyzer 76 is turned on to circulate the water to the analyzer. The temperature of the dissolution water 12 within the dissolution chamber 22 is then measured by the temperature probe 68. This enables the system to reach equilibrium or "equilibrate." The analyzer is then set to zero.

A standard sample of the pharmaceutical making up the dosage form to be tested is then prepared for calibrating the analyzer 76. To that end, a sample solution of the product(s) that will be tested is run through the analyzer, e.g., the spectrophotometer 76, to get a absorbence measurement to be used as the standard. In particular, the standard solution is pumped for a period of time, e.g., five minutes, through the inlet line 84 to the spectrophotometer 76, where readings are taken, and from the spectrophotometer to the outlet line 88. The outlet line 88 is at this time directed into a waste container (not shown) to collect the sample solution for disposal. The running of the sample solution through the analyzer enables one to get a true and accurate measure of the amount of the active ingredient(s) in the standard solution. The lines 80 and 88 to and from the spectrophotometer are then washed out to ensure that none of the standard solution remains in them or in the spectrophotometer 76. Once that has been accomplished the lines 80 and 88 are reconnected to the reservoir 24 and the pump 82 is restarted to carry the dissolution liquid, e.g., water, back through the spectrophotometer 76 to equilibrate it again.

The system is now ready for the dissolution test of the dosage form(s). To that end, the user weighs out a known weight, e.g., 100 mg, of plural of the dosage forms to be tested. These dosage forms are then transferred onto the support mesh 136. Preferably the amount of dosage forms that are weighed out will be such as to only form a single layer on the mesh (such as shown in FIG. 3) so that all the dosage forms can be imaged by the camera. In fact, it is desirable that the plural dosage forms being tested are isolated from each other physically on the support mesh, so they do not touch one another's sides. The best images of the dosage forms can be obtained when each dosage form is not immediately adjacent to another dosage form to impede the visibility of its surface. This is made more difficult by filling the support mesh completely with dosage forms. Accordingly, it is preferred that the entire surface of the support mesh 136 not be covered with dosage forms, e.g., only half of the mesh is filled. If the amount of dosage forms to be tested would be too many for a single support mesh to viably accommodate and a minimum amount of the drug is required in order for the dissolution analysis to be accurate, a second mesh support can be used to split up the plural dosage forms onto two groups within the dissolution chamber. In such a case the dissolution chamber includes a second mesh support located diametrically opposite to the first support mesh and supported on plural spherical legs in the same manner as the first support mesh. The plural dosage forms can then divided up between the first support mesh (the one in the visualization field) and the second support mesh. Since there will be sufficient dosage forms on the first support mesh for visualization by the imaging means, there is no requirement to visually record the dosage forms on the second mesh.

After the dosage forms are placed on the mesh, the evaporation cover 60 of the dissolution chamber 22 is then removed to provide access to the interior of the chamber and the mesh 136 with the dosage forms 10 thereon is then carefully introduced into position in the chamber. To that end, some means, e.g., a spatula, may be used to hold the dosage forms on the mesh as the mesh is gently lowered into the dissolution liquid. This prevents displacement of any of the dosage forms if they would have a tendency to float during immersion.

The system is started, e.g., the start button 120 is depressed at the moment that the dosage forms on the mesh become submerged in the dissolution liquid. The evaporation lid 60 is then replaced on the dissolution chamber 22. The stereo-microscope 100 and camera 98 are then checked to make sure that the dosage 10 forms within the visualization field are sharply in focus through the transparent dissolution liquid, e.g., the water. Once this has been accomplished an input can be entered into the computer 38 to cause the video camera 98 to commence operation and to cause the photo-printer 104 to produce a hard copy photograph of the condition of the dosage forms at the start of the test. The inherent delay, e.g., approximately 15 seconds, between the start of the system and the start of the video recording should not present any problem from the standpoint of accuracy of the testing. This delay can be reduced to almost zero if the system 20 is fully automated.

Once the system starts, the video camera 98 provides a series of sequential images of the dosage forms 10 as they dissolve at the same time that the analyzer 76 is providing its data the computer 38 until the test is deemed over. In particular, in the exemplary embodiment shown the spectrophotometer 76 electronically measures the amount of light absorbed by the dissolution liquid sample 12, e.g., water, flowing past the spectrophotometer's sensor and provides an output signal indicative of that light absorbency to the computer 38 via lines 78. The computer takes that data and compares it against the data previously input into it from the spectrophotometer reading the standard solution preceding the test run. Based on a comparison of the weights and the absorbancies of the sample solution to the standard solution, the computer 38 calculates the percentage release of the active ingredient(s) from the sample. This data is stored in the computer for subsequent analysis by the user of the system to correlate the dissolution data with the images at any time during the test that the user desires to consider. Hard copies of the results of the analysis can be provided by the printer 116. In particular, the system can provided hard copy images or photographs showing the state of dissolution of the dosage forms at any time during the dissolution test, with indicia printed thereon indicating the elapsed time from the start of the test and the percentage of the active ingredient(s) dissolved, e.g., "elapsed time: 10 minutes and 30 seconds; 12% dissolution."

One of the significant advantages of this invention is that the imaging means can provide a high quality image of either the whole visualization field or only small portion of it. This feature enables a person (or an automated image morphology analysis system) to examine the details of the surface of selected, e.g., one or more, dosage forms within the entire visualization field. Examining such surface details can be of considerable importance in testing dosage forms making use of a shell containing the active ingredient(s), where the outer shell is a polymer coating designed to remain intact for the total of the dissolution run, while the active ingredient(s) is(are) supposed to diffuse through that coating into the dissolution liquid. For example, if in an hour's time there is 40% release of active ingredient(s) and the image shows the coating is intact, without any blisters or ruptures, this indicates that the formulation appears to be working as designed. If at the end of the test, e.g., after eight hours time, you have 100% released and the image at that time still shows no blisters or ruptures, i.e., the formulation coating is still perfect, one can conclude that the formulation has, in fact, worked as designed. If, for example, on the other hand after 15 minutes one gets an image showing the coating is perfect, but there is very little drug release, e.g., 1% drug release, yet the image of the dosage forms taken at forty-five minutes shows that the shell or coating of the formulation has ruptured and the active ingredient dissolved in the dissolution liquid has abruptly reached 60%, the user of the system can accurately draw the inference that the mechanism of drug release in that formulation is by rupture and not by diffusion. Thus, the system of this invention can be a valuable diagnostic tool to ensure that the formulation acts in its designed manner.

It should be pointed out at this juncture that the subject invention is not limited to use for time release or coated formulations. The system can be used with un-coated products which are designed for immediate release. Moreover, the system can be used to take photographs and analyze multi-drug release at selected intervals, e.g., every 60 seconds. From the data and photographs one can accurately determine how the pharmaceutical product behaves. For example, in some formulations one might have some gas bubbles produced because of a chemical interaction which wouldn't be seen in any other apparatus that's currently available and that may be of concern to organic chemists who feel that there should be no gas bubble generation from the drug. So too, the system can be used for determining the action of transdermal patch formulations. In this regard most transdermals have a gel membrane over the gel formulation in the center of the patch. Thus, images showing membrane changes, e.g., small tears or ruptures, pieces breaking off, etc., that are provided by this system can prove invaluable to determine the viability of the formulation.

Without further elaboration the foregoing will so fully illustrate my invention that others may, by applying current or future knowledge, adopt the same for use under various conditions of service.

I claim:

1. Apparatus for monitoring the dissolution properties of a solid dosage form containing at least one active ingredient, said apparatus comprising a dissolution chamber, video monitoring means, and dissolution liquid analyzing means, said dissolution chamber comprising a hollow vessel having an interior in which a dosage form support is located and an inlet and outlet coupled to the interior of said chamber, said dosage form support being arranged to support the dosage form within a predetermined visualization field in said chamber, said inlet of said chamber being adapted to enable a dissolution liquid to flow gently through the interior of said chamber for exposure to the dosage form, said support and said gentle flow of the dissolution liquid tending to prevent displacement of said dosage form from said visualization field, said flow of dissolution liquid causing the dosage form to dissolve in the dissolution liquid, said outlet of said chamber being coupled to said analyzing means for carrying the dissolution liquid to said analyzing means for analyzing the properties of the dissolution liquid, said video monitoring means being adapted for aiming at said visualization field to provide a series of high quality images of the dosage form simultaneously with the analysis of the dissolution liquid by said analyzing means, said apparatus further comprising a baffle arranged for diverting the flow of the dissolution liquid entering into said chamber so that the entering dissolution liquid does not directly impact the dosage form in said visualization field, thereby providing said gentle flow and not interfering with the imaging of the dosage forms during the flow of said dissolution liquid.

2. The apparatus of claim 1 additionally comprising a printer for printing hard copies of selected ones of said series of images.

3. The apparatus of claim 1 further comprising a recorder coupled to said video monitoring means for recording the images of the solid dosage form.

4. The apparatus of claim 1 wherein said analyzing means is selected from the group consisting of spectrophotometric and high performance liquid chromatography equipment.

5. The apparatus of claim 1 wherein said apparatus additionally comprises a computer coupled to said analyzer means.

6. The apparatus of claim 1 wherein said dosage form support comprises a mesh.

7. The apparatus of claim 6 wherein said mesh is arranged to support plural of the dosage forms and wherein said video monitoring means is arranged to provide said images of the plural dosage forms simultaneous with the analysis of the dissolution liquid by said analyzing means.

8. The apparatus of claim 1 wherein said baffle comprises an arcuate wall against which a stream of the dissolution liquid is directed from said inlet of said chamber.

9. The apparatus of claim 8 wherein said dosage form support comprises a mesh and wherein said arcuate wall tends to block the stream of the dissolution liquid from directly impacting the dosage supported by said mesh.

10. The apparatus of claim 9 wherein said dissolution chamber comprises a generally disk-like vessel having a circular sidewall and a generally planar bottom wall, said mesh being located above said bottom wall.

11. The apparatus of claim 10 wherein said inlet is located within said sidewall and wherein said outlet is located within said sidewall disposed diametrically opposite to said inlet.

12. The apparatus of claim 11 wherein said baffle is located between said inlet and said outlet and adjacent to said inlet, and wherein said mesh is located adjacent said sidewall approximately midway between said inlet and said outlet and laterally from the center of said chamber.

13. The apparatus of claim 1 wherein said dissolution liquid within said dissolution chamber has an upper surface through which the image of the dosage form is acquired by said video monitoring means, said chamber being constructed so that the upper surface of the dissolution liquid is substantially even, so that said video monitoring means can acquire a high quality image of the solid dosage form submerged within the dissolution liquid below the upper surface.

14. The apparatus of claim 13 additionally comprising a reservoir of the dissolution liquid coupled to said inlet of said dissolution chamber and temperature control means for controlling the temperature of the dissolution liquid, said temperature control means comprises first and second liquid jackets into which a temperature controlled liquid is introduced, said first jacket being located contiguous with at least a portion of said dissolution chamber, said second jacket being located contiguous with at least a portion of said reservoir.

15. The apparatus of claim 1 additionally comprising temperature control means for controlling the temperature of the dissolution liquid.

16. The apparatus of claim 15 wherein said temperature control means comprises a liquid jacket into which a temperature controlled liquid is introduced, said jacket being located contiguous with at least a portion of said dissolution chamber.

17. The apparatus of claim 15 wherein said temperature control means comprises first and second liquid jackets into which a temperature controlled liquid is introduced, said first jacket being located contiguous with at least a portion of said dissolution chamber, said second jacket being located contiguous with at least a portion of said reservoir.

18. The apparatus of claim 15 wherein said dissolution chamber additionally comprises an evaporation cover.

19. The apparatus of claim 18 wherein said evaporation cover is temperature controlled.

20. The apparatus of claim 1 additionally comprising a reservoir of the dissolution liquid coupled to said inlet of said dissolution chamber.

21. The apparatus of claim 20 additionally comprising temperature control means or controlling the temperature of the dissolution liquid.

22. The apparatus of claim 20 wherein said reservoir additionally comprises an evaporation cover.

23. The apparatus of claim 1 wherein said dissolution chamber additionally comprises an evaporation cover.

24. The apparatus of claim 23 wherein said evaporation cover includes at least one transparent portion to enable said video monitoring means to acquire the images of the solid dosage form therethrough.

25. The apparatus of claim 1 wherein said video monitoring means additionally comprises a stereo-microscope for providing enlarged stereo images of the dosage form as it dissolves.

26. The apparatus of claim 25 further comprising a recorder coupled to said video monitoring means for recording the images of the solid dosage form.

27. The apparatus of claim 1 additionally comprising a reservoir for the dissolution liquid, and a first pump, said reservoir being in fluid communication with said pump, said pump being in fluid communication with said reservoir and said inlet to provide the dissolution liquid to said chamber, and said reservoir being in fluid communication with said outlet to receive the dissolution fluid from said chamber.

28. The apparatus of claim 27 additionally comprising a second pump in fluid communication with said reservoir to provide a sample of the dissolution liquid to said analyzing means.

29. The apparatus of claim 28 additionally comprising stirring means for stirring the dissolution liquid in said reservoir.

30. The apparatus of claim 1 wherein said dissolution liquid within said dissolution chamber has a surface through which the image of the dosage form is acquired by said video monitoring means, said chamber being constructed so that the surface of the dissolution liquid is substantially non-turbulent so that said video monitoring means can acquire a high quality image of the solid dosage form through said surface of said dissolution liquid.

31. A method for monitoring the dissolution properties of a solid dosage form containing at least one active ingredient, said method comprising:
(A) disposing said solid dosage form in a chamber at a predetermined location forming a visualization field;
(B) providing a flow of dissolution liquid into said chamber through said visualization field for dissolving said dosage form, said flow of dissolution liquid being diverted after entering into said chamber and prior to flowing through said visualization field so as to prevent said flow of fluid entering said chamber from directly impacting and displacing the dosage form;
(C) analyzing said dissolution liquid as said dosage form dissolves to determine the dissolution properties of said dosage form; and
(D) simultaneously recording a series of high quality images of said dosage form as it dissolves in said dissolution liquid.

32. The method of claim 31 additionally comprising controlling the temperature of said dissolution liquid.

33. The method of claim 31 wherein said temperature is held constant.

34. The method of claim 31 wherein said dissolution liquid is introduced into said chamber at a controlled flow rate.

35. The method of claim 31 wherein said analysis of said dissolution liquid is accomplished by withdrawing at least a portion of said dissolution liquid from said chamber.

36. The method of claim 31 wherein plural solid dosage forms are monitored simultaneously and wherein said images are of at least some of said plural dosage forms.

37. The method of claim 31 additionally comprising recording the dissolution properties of the dosage form as determined by said analysis and correlating said dissolution properties and said recorded images.

38. The method of claim 31 additionally comprises providing hard copy prints of at least selected ones of said series of images.

39. The method of claim 31 wherein said analysis is selected from the group consisting of spectrophotometry or high performance liquid chromatography.

40. The method of claim 31 wherein the flow of liquid is diverted in step B by directing the flow entering said chamber against a baffle.

41. The method of claim 31 wherein at least one parameter of the composition of said dissolution liquid is changed during the dissolution of said dosage form.

42. The method of claim 41 wherein the at least one parameter changed is the pH of said dissolution liquid.

43. The method of claim 41 additionally comprising controlling the temperature of said dissolution liquid.

44. A method for monitoring the dissolution properties of a solid dosage form, said method comprising:
(A) disposing said solid dosage form in a chamber at a predetermined location forming a visualization field;
(B) providing a flow of dissolution liquid into said chamber for dissolving said dosage form;
(C) slowing the velocity of the dissolution liquid flowing through said visualization field relative to said dosage form so that the dosage form is not displaced, said slowing being carried out by spreading out the flow of dissolution liquid after it enters said chamber and before it reaches said dosage form;
(D) analyzing said dissolution liquid as said dosage form dissolves to determine the dissolution properties of said dosage form; and
(E) simultaneously recording a series of high quality images of said dosage form as it dissolves in said dissolution liquid.

45. The method of claim 44 wherein the flow of dissolution liquid is spread out by diverting the flow of dissolution liquid entering said chamber.

46. The method of claim 44 wherein the flow of dissolution liquid is spread out by directing the flow of dissolution liquid entering said chamber against a baffle, said dissolution liquid spreading out as it flows around said baffle.

* * * * *